United States Patent
Funk et al.

(10) Patent No.: US 9,918,810 B2
(45) Date of Patent: Mar. 20, 2018

(54) METHOD FOR PRODUCING A DENTAL PROSTHESIS WITH A TEMPLATE

(71) Applicant: Heraeus Kulzer GmbH, Hanau (DE)

(72) Inventors: Matthias Funk, Hanau (DE); Jochen Sagolla, Frankfurt am Main (DE); Helmut Redemann, Frankfurt am Main (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 15/532,174

(22) PCT Filed: Dec. 4, 2015

(86) PCT No.: PCT/EP2015/078718
§ 371 (c)(1),
(2) Date: Jun. 1, 2017

(87) PCT Pub. No.: WO2016/091762
PCT Pub. Date: Jun. 16, 2016

(65) Prior Publication Data
US 2017/0265971 A1  Sep. 21, 2017

(30) Foreign Application Priority Data
Dec. 9, 2014 (DE) .................. 10 2014 118 231

(51) Int. Cl.
*G06F 19/00* (2018.01)
*A61C 13/00* (2006.01)
(Continued)

(52) U.S. Cl.
CPC ...... *A61C 13/0004* (2013.01); *A61C 13/0022* (2013.01); *A61C 13/09* (2013.01); *A61C 13/08* (2013.01)

(58) Field of Classification Search
CPC combination set(s) only.
See application file for complete search history.

(56) References Cited

U.S. PATENT DOCUMENTS 4,354,900 A * 10/1982 Bailey ............... C25B 13/04
  162/106
4,663,720 A *  5/1987 Duret ............... A61C 9/00
  433/214

(Continued)

FOREIGN PATENT DOCUMENTS

DE        10304757 B4     7/2005
DE    102009056752 A1     6/2011
(Continued)

OTHER PUBLICATIONS

Search Report in International Application No. PCT/EP2015/078718 dated Feb. 5, 2016, 6 pages.
(Continued)

*Primary Examiner* — Kidest Bahta
(74) *Attorney, Agent, or Firm* — Marshall, Gerstein & Borun LLP

(57) ABSTRACT

The invention relates to a method for producing a dental prosthesis, wherein the dental prosthesis comprises a prosthesis base and a plurality of prosthesis teeth, wherein the method is carried out making use of a virtual three-dimensional dental prosthesis model of the physical dental prosthesis which is to be produced, and wherein the virtual three-dimensional dental prosthesis model comprises virtual prosthesis teeth and a virtual prosthesis base, with the steps:
from the external form of the vestibular surfaces and/or occlusal surfaces of the virtual prosthesis teeth, and from the external form of the vestibular surface of the virtual prosthesis base of the virtual three-dimensional dental prosthesis model, a virtual model of a template is calculated, such that a region of the virtual surface of the virtual template is formed by a negative of the vestibular surfaces and/or occlusal surfaces of the virtual prosthesis teeth and of the virtual prosthesis base, wherein the location and the orientation of the virtual (Continued)

prosthesis teeth relative to one another and relative to the virtual prosthesis base remain retained in the negative;

producing of a physical template with a CAM method on the basis of the data of the virtual model of the template;

placing and securing of physical prosthesis teeth in the template, wherein the vestibular surfaces and/or occlusal surfaces of the prosthesis teeth are placed in the surface of the template formed by the negative matching thereto; and securing the physical prosthesis teeth to a physical prosthesis base, wherein the prosthesis base is inserted into the template fitted with the prosthesis teeth, such that the vestibular surface of the prosthesis base is placed in the matching surface of the template formed by the negative.

25 Claims, 5 Drawing Sheets

(51) Int. Cl.
  *A61C 13/09* (2006.01)
  *A61C 13/08* (2006.01)

(56) References Cited

U.S. PATENT DOCUMENTS 9,295,534 B2  3/2016  Ruppert et al.
2004/0219490 A1  11/2004  Gartner et al.
2007/0287131 A1*  12/2007  Ruppert ............ A61C 13/0004
    433/223
2014/0087327 A1  3/2014  Noack
2014/0272796 A1*  9/2014  Grobbee ............ A61C 13/1006
    433/199.1
2015/0066181 A1  3/2015  Beyer et al.
2015/0216638 A1*  8/2015  Baaske .................. A61C 13/00
    433/196
2016/0008180 A1*  1/2016  Piantoni ............ A61F 13/15617
    425/80.1
2016/0193019 A1  7/2016  Heinz et al.

FOREIGN PATENT DOCUMENTS

DE       102012007706 A1   10/2013
EP            2030590 A1    3/2009
EP            2666438 A2   11/2013
EP            2571451 B1    3/2014
EP            2742906 A1    6/2014
JP           09-238960      9/1997
WO        WO-91/07141 A1    5/1991
WO     WO-2013/0124452 A1   8/2013

OTHER PUBLICATIONS

International Preliminary Report on Patentability and Written Opinion in International Application No. PCT/EP2015/078718 dated Jun. 13, 2017, 7 pages.

* cited by examiner

METHOD FOR PRODUCING A DENTAL PROSTHESIS WITH A TEMPLATE

BACKGROUND OF THE INVENTION

Field of the Invention

The invention relates to a method for producing a dental prosthesis, wherein the dental prosthesis comprises a prosthesis base and a plurality of prosthesis teeth, wherein the method is carried out making use of a virtual three-dimensional dental prosthesis model of the physical dental prosthesis which is to be produced, and wherein the virtual three-dimensional dental prosthesis model comprises virtual prosthesis teeth and a virtual prosthesis base.

The invention also relates to a dental prosthesis produced with such a method, a device or combination of devices for carrying out such a method, and a template produced with a CAD/CAM process for implementing such a method.

Related Technology

The conventional procedure is the analog production of dental prostheses. To produce the prosthesis base, in most cases an analog process is used in which first an impression is taken of the toothless jaw of the patient. From this impression, a plaster model of the patient's situation is prepared. Next, a function model of the prosthesis made of wax is built up on the plaster model and fitted with prosthesis teeth. A hollow mold or casting mold is then built up from these two parts, in which the prosthesis teeth are already integrated. As a result of this, the prosthesis teeth are already inserted into the hollow mold. The mold is cast in a plastic which is the color of the gum, and during the casting process the prosthesis teeth are bonded to the prosthesis base. Once the plastic has cured it undergoes further working in order to obtain the desired shape. With this technique, a preliminary ridge or even a preliminary casting made of silicone or plaster is used for the fixing and positioning of the prosthesis teeth.

For producing the dental prosthesis, prosthesis teeth are positioned manually and individually on a wax base on a plaster model of the toothless jaw. In the next step, this wax prosthesis is embedded in a flask with plaster, silicone, or gel (depending on the later processing technique), in order then, after the hardening of the embedding material, to release the wax base from the mold, in order to create a cavity for the prosthesis plastic. In this situation the prosthesis teeth remain in the embedding material. An appropriate plastic is then injected or cast into the cavity, as a result of which, after the curing of the plastic, the dental prosthesis is obtained. When the prefabricated artificial teeth are positioned, they are adjusted and ground to match the individual mouth situation of the patient by the dental technician, and, if appropriate, also by the dentist.

As well as manual craft techniques, digital manufacturing methods are increasingly gaining in importance in the dental sector. Dental restoration work, such as crowns and bridges, has for some years been produced in a subtractive manner with milling procedures by means of CAD/CAM technologies (CAM—Computer-Aided Manufacturing, CAD—Computer-Aided Design).

A CAD/CAM process for producing a dental prosthesis is known from WO 91/07141 A1, wherein, with this process, prosthesis base is milled out of a plastic block on the basis of an impression.

In addition, generative CAM processes such as SLM (Selective Laser Melting) are steadily growing in importance for the production of crowns, bridges, and models, as well as stereolithography and DLP (digital light processing) for dental products on a polymer base, such as, for example, temporary fittings, prostheses, gnatho-orthopedic apparatus, bite guards, drill templates or dental models. In this context, the production of dentures on an acrylate base by means of RP processes (Rapid Prototyping processes) has hitherto been subjected to increasingly tight restrictions. Multicolored dentures or dentures made from a variety of different polymer materials (such as for enamel and dentine compounds) for the production of high-quality and aesthetic dentures have hitherto only been feasible by means of elaborate and expensive RP machines with multiple material chambers, or by means of adhesive bonding and jointing techniques.

Likewise, the production of material combinations (such as CoCr and polymer) by means of RP processes has hitherto been very elaborate and expensive, and has not been put into large-scale effect. The generative production of aesthetically demanding artificial teeth for partial or total prostheses is not possible at the present time, since by means of stereolithography only one material or one color can be printed. The printing of multicolored artificial teeth is not possible at the present time. For this reason, the prosthesis base is produced by means of CAM processes (such as milling or printing) and prefabricated artificial prosthesis teeth are adhesively bonded to the prosthesis base.

There are already preliminary methods, such as the methods known from DE 10 2009 056 752 A1 or WO 2013 124 452 A1, with which a dental part or total prosthesis is created digitally and produced by CAD/CAM processes. EP 2 742 906 A1 discloses a method with which a dental arch is connected to a mold-making compound material, wherein the compound is contained in an individualized impression tray, and contains an impression of the oral cavity situation of the patient. The surface of the mold with the dental arch is digitalized and then, by means of computerized techniques, a virtual model of the dental arch is positioned and oriented as accurately as possible in the virtual model of the prosthesis base. During the subsequent production, the prosthesis teeth must be individually and manually checked for a correct match in the tooth sockets provided in the prosthesis base in order for them to be subsequently adhesively bonded in place, wherein, as the instrument for carrying out the check, a transfer template can be used. From DE 103 04 757 B4 a method is known for producing dentures with which a virtual arrangement of the teeth into a virtual model is carried out, and the production of a prosthesis base is then carried out on the basis of the virtual model.

With regard to the production of removable dentures, such as full and part prostheses, which were produced with the aid of digital data with a CAD design, there are technical solution concepts for separating the data of the prosthesis base and the teeth. The prosthesis base can in this situation be produced by an additive or also subtractive production process. As prosthesis teeth, consideration can be given to artificial plastic teeth or also individually produced prosthesis teeth or dental arches from the same production processes as the prosthesis base. In every case, tooth sockets must be provided in the prosthesis base to accommodate these prosthesis teeth, into which, in a subsequent manual production step, the prosthesis teeth or dental arches are secured, for example by adhesive bonding.

The difficulty in this situation is to transfer the arrangement and alignment of the teeth produced by digital means to the prosthesis base into the manual production step. Because the tooth sockets in the prosthesis base in most cases cannot be arranged as very deep, the teeth which are inserted do not have sufficient guidance for a rotation and tilt movement to be possible in the oral or lingual direction of each individual prosthesis tooth, or of the prosthesis teeth in relation to one another with regard to the dental interspaces. A freehand positioning of the prosthesis teeth therefore has nothing more to do with the structural setting and matching of the prosthesis teeth in the upper and lower jaw in the digital data record.

Such methods have the disadvantage that the prosthesis teeth must be treated or removed occlusally, wherein the prosthesis base is subsequently ground or the prosthesis teeth are basally ground, in order for their position and setting to be adjusted. In most cases, the prefabricated prosthesis teeth which provide the best aesthetic results are basally shortened before the adhesive bonding, in order to adjust the height of the bite (the occlusion) of the dental prosthesis, such that the need arises to provide a rational and economical method and process.

From EP 2 571 451 B1 and EP 2 666 438 A2 methods are known with which prosthesis teeth are embedded in a retaining element in wax and then undergo basal milling. The milled prosthesis teeth are released from the wax and then inserted into a prosthesis base and adhesively bonded there in order to produce a dental prosthesis.

These methods have the disadvantage that the prosthesis teeth must be treated individually or in groups and inserted and bonded individually into the prosthesis base. The correct location for the insertion of the prosthesis teeth into the prosthesis base must in this situation be determined by trial and error. The basal form to match the prosthesis teeth must be calculated for each prosthesis tooth. As well as this, the locations and orientations of the individual prosthesis teeth in the wax block must be determined in order for them to be basally abraded with a fully automatic computer-controlled milling process. With such methods, erroneous settings of prosthesis teeth in the prosthesis base may occur, or these erroneous settings must be prevented by additional measures.

SUMMARY

The object of the invention therefore consists of overcoming the disadvantages of the prior art. In particular, a method is to be provided with which a simple and rapid production of the dental prosthesis can be carried out. In this situation, it is intended that modern computer-controlled processes can be applied, and existing data and techniques can be used to the greatest extent possible. As well as this, it is intended that the prosthesis teeth should as far as possible be secured without any erroneous setting in the previously calculated orientation and location in the prosthesis base.

With the manual shortening of artificial prosthesis teeth, the problem also arises that the basal side (the cervical region) of the prosthesis teeth to be produced exhibits an individual geometry, and before the milling or printing of the prosthesis base this geometry must be scanned in accordingly and the matching counter-piece for the prosthesis base constructed. This incurs extra effort and expenditure.

The objects of the invention are solved by a method for producing a dental prosthesis, wherein the dental prosthesis comprises a prosthesis base and a plurality of prosthesis teeth, wherein the method is applied with the use of a virtual three-dimensional dental prosthesis model of the physical dental prosthesis which is to be produced, and wherein the virtual three-dimensional dental prosthesis model comprises virtual prosthesis teeth and a virtual prosthesis base, characterized by the following chronological steps:

A) From the external shape of the vestibular surfaces and/or occlusal surfaces of the virtual prosthesis teeth, and from the external form of the vestibular surface of the virtual prosthesis base of the virtual three-dimensional dental prosthesis model, a virtual model of a template is calculated, such that a region of the virtual surface of the virtual template is formed by a negative of the vestibular surfaces and/or occlusal surfaces of the virtual prosthesis teeth and of the virtual prosthesis base, wherein the location and the orientation of the virtual prosthesis teeth relative to one another and relative to the virtual prosthesis base remain retained in the negative;

B) Production of a physical template with a CAM process on the basis of the data of the virtual model of the template;

C) Placement and securing of physical prosthesis teeth in the template, wherein the vestibular surfaces and/or occlusal surfaces of the prosthesis teeth are placed in the surface of the template which is formed by the matching negative; and D) Securing of the physical prosthesis teeth to a physical prosthesis base, wherein the prosthesis base is inserted into the template fitted with the prosthesis teeth, such that the vestibular surface of the prosthesis base is located on the matching surface of the template formed by the negative.

The term "occlusal" signifies the positional and directional designation of the teeth on the occlusion surface or masticatory surface and towards the other occlusion surface. The designation "vestibular" signifies towards the vestibular trough (labial or buccal). These terms are also used for prosthesis teeth.

With the method according to invention, it can be provided that the virtual three-dimensional dental prosthesis model is divided by computer calculation, by means of file-splitting, into a three-dimensional model of the virtual prosthesis teeth and a virtual three-dimensional model of the prosthesis base.

In this situation it can preferably be provided that, at the division of the virtual dental prosthesis model, dental alveolae or sockets can be calculated for locating into the virtual model of the prosthesis base, which match with the basal sides of the virtual model of the prosthesis teeth, such that the form of the virtual model of the prosthesis base can be connected flush-surface to the form of the basal sides of the virtual model of the prosthesis teeth, or located flush-surface in contact with one another.

By way of these measures the situation is achieved that the forms of the prosthesis base and prosthesis teeth produced with the aid of the virtual models match precisely to one another and can be secured matching and flush-surface, and therefore in a stable manner, into one another, and that, respectively, the physical prosthesis teeth which are produced or treated following the virtual model of the prosthesis teeth can be connected flush-surface with the tooth sockets of the physical prosthesis base.

It can further be provided that the virtual model of the template is additionally calculated from the external form of the vestibular surface of a model of the oral cavity situation of the patient, such that a region of the virtual surface of the virtual template is formed by a negative of at least one region of the vestibular surface of the model of the oral cavity situation, wherein the location and the orientation of the virtual prosthesis teeth and of the virtual prosthesis base relative to the model of the oral cavity situation, with the virtual prosthesis base based on the model of the oral cavity situation, remains retained in the negative.

The model of the oral cavity situation can be produced either with the aid of an intraoral scan, with the aid of a wax or a silicone impression, which was then subsequently scanned in, or with the aid of a plaster model of the oral cavity situation, which was then scanned in. The model of the oral cavity situation is necessary from the outset for dental prostheses produced by CAD/CAM in order to determine the location of the prosthesis base in the toothless, or toothless in part, saddle of the patient's jaw. From the virtual model of the oral cavity situation, a physical model of the oral cavity situation is then produced with a CAM process, onto which the prosthesis base can be placed.

The model of the oral cavity situation of the patient can in this situation comprise a base which does not correspond to the oral cavity situation of the patient, and is built up on the form of the oral cavity situation. The base of the model of the oral cavity situation can be built up as a continuation of the side of the oral cavity situation facing away from the dental arch. This prolongation, or base respectively, of the dental arch, which does not accord with any real correspondence in the oral cavity situation, is then preferably provided for the adjustment of the template. As a result, a larger vestibular connection surface of the model of the oral cavity situation to the template can be achieved, such that an easier and more exact positioning of the prosthesis teeth in the prosthesis base is possible.

With a further embodiment of the invention it is proposed that in step D) the securing of the physical prosthesis teeth in the physical prosthesis base takes place in such a way that the prosthesis base and the physical model of the oral cavity situation of the patient are inserted into the template fitted with the prosthesis teeth, such that the vestibular surface of the prosthesis base and the vestibular surface of the physical model of the oral cavity of the patient are located on the surface of the template formed by the negative.

Preferably the physical model of the oral cavity of the patient corresponds to the virtual model of the oral cavity at least with regard to the connection surfaces to the prosthesis base and with regard to the connection surfaces to the template. As a result, a large connection surface between the physical model of the oral cavity situation and of the prosthesis base and the prosthesis teeth can be used for the positioning of the prosthesis teeth in the prosthesis base. In this situation, the direction indication of vestibular in respect of the model of the oral cavity is also used for a base of the model of the oral cavity which does not have any correspondence in the oral cavity situation of the patient, but only surfaces which are aligned in the same way as with the patient's real oral cavity situation. Preferably, no intermediate space remains between the connection surface of the prosthesis base and the prosthesis teeth to the template, and/or between the prosthesis base and the model of the oral cavity situation to the template. This can be achieved in that the boundary lines between the prosthesis base and the prosthesis teeth and/or between the prosthesis base and the model of the oral cavity situation remain retained as negatives on the surface of the template.

According to a further embodiment of the present invention, it can also be provided that, in respect of the negative of the vestibular surface of the model of the oral cavity situation, by computer calculation, at least one indexing, and preferably at least three indexings, is added to the virtual model of the template, and to the vestibular surface of the model of the oral cavity situation, by computer calculation, a matching negative of the surface of the at least one indexing is added to the model of the oral cavity situation, preferably matching negatives of the at least three indexings to the model of the oral cavity situation.

As a result of this, an erroneous orientation of the template and therefore of the prosthesis teeth on the prosthesis base can be avoided. As an alternative, however, the form of the model of the oral cavity situation can be determined in its entirety, even without local indexing, in such a way that an exact and unambiguous positioning of the template in relation to the model of the oral cavity situation is possible.

Preferred embodiments of the method according to the invention can be characterized in that, by computer calculation, at least one indexing, and preferably at least three indexings, can be added to the negative of the vestibular surface of the virtual prosthesis base, in respect of the virtual model of the template, and to the vestibular surface of the virtual prosthesis base, by computer calculation, a matching negative of the at least one indexing is added, preferably matching negatives of the at least three indexings.

As indexings, cut-outs or elevations can be provided or produced as geometric bodies on the surface of the prosthesis base, of the physical models of the oral cavity situation, and, as a negative to these, on the template. With the aid of the indexings, an exact and unambiguous positioning of the template to the physical prosthesis base and/or to the physical model of the oral cavity situation is possible. Due to the indexing, a latching engagement to the physical prosthesis base and/or to the physical model of the oral cavity situation can be attained, which engages in a counter-latch arrangement (namely the negative indexing) on the template, such that the correct positioning of the template can be easily carried out. As an alternative, the form of the prosthesis base can also be determined without local indexings in its entirety, in such a way that an exact positioning of the template to the prosthesis base is possible.

It can also be provided that, after step D), the template of the finished dental prosthesis, consisting of the prostheses teeth secured in the prosthesis base, is removed.

With this, the method is concluded and the dental prosthesis which has been produced is then present as an individual element. By way of this step it is intended to make it clear that the template is not permanently connected to the prosthesis teeth and the prosthesis base. Contrary to this, it is intended that the prosthesis teeth should finally be permanently connected to the prosthesis base, in order to create the dental prosthesis. In addition or as an alternative, it can also be provided that, with the template, a temporary tooth arrangement and fixing in the prosthesis base is carried out, in order to allow the dentist to offer up the arrangement as a test, with the possibility of correction. In this case, it is only in a subsequent step that the final permanent assembly is carried out.

It can further be provided that the virtual three-dimensional dental prosthesis model is produced on the basis of an intraoral scan, in order to provide the form of the virtual prosthesis base, and by a virtual arrangement of virtual models of artificial prosthesis teeth in the virtual prosthesis base, wherein preferably the form, the location, and/or the orientation of the prosthesis teeth is selected by a simulation of the location of the dental prosthesis in the oral cavity of the patient and/or by a simulation of the location and orientation of the prosthesis teeth to one another and/or to the prosthesis base, wherein particularly preferably the occlusion plane and/or the mastication movements of the oral cavity are simulated.

As a result of this, a further automation of the method is achieved. Since, for the virtual model of the template, a virtual dental prosthesis model is required in any event, such a production of data for the virtual models is particularly advantageous. By way of the measures described, a high degree of variability of the method is obtained, and thereby a particularly individual and therefore accurate adjustment of the dental prosthesis is achieved.

According to a further embodiment, it can be provided that the physical prosthesis base and the physical template are produced and/or processed with CAM procedures, in particular with rapid-prototyping methods, based on the virtual models.

As a result, the virtual models necessary for the method can also be used simultaneously for the rapid and automated production of the prosthesis base.

It can also be provided that the physical prosthesis teeth inserted into the template undergo basal processing before they are secured to the physical prosthesis base. Preferably, the artificial prosthesis teeth based on the virtual model of the prosthesis teeth are basally abraded with a CAM process, and for particular preference are basally abraded by computer-controlled milling, before they are secured to the physical prosthesis base.

In this situation, for particular preference a computer-controlled CAM milling cutter is used, such as a computer-controlled 4-axis or 5-axis cutter. As a result, an adjustment of the prosthesis teeth to the prosthesis base can be carried out, such that the dental prosthesis which is produced can be built up in a particularly stable and variable manner.

With such methods it can also be provided that the prosthesis teeth are abraded on the basis of the virtual models of the prosthesis teeth with a CAM process, in particular by milling, such that the basal form of the prosthesis teeth is adjusted to tooth sockets for the prosthesis teeth in the prosthesis base in such a way that the external form of the prosthesis base corresponds to the inserted prosthesis teeth of the external form of the virtual dental prosthesis model.

Preferably, the prosthesis teeth are adjusted by the basal abrading to the arrangement of tooth sockets for the prosthesis teeth in the prosthesis base. The prosthesis teeth can then be inserted or laid without any problem into these sockets with their basal sides, which are located opposite the coronal sides of the prosthesis teeth, and which, due to the basal abrading of the prosthesis teeth, are matched to the arrangement of tooth sockets of the prosthesis base.

It can also be provided that the prosthesis teeth are produced with a CAM process, preferably by milling or a build-up CAM process.

As a result, a further automation of the method can be achieved, with which the data available can advantageously be applied as widely as possible.

It can further be provided that, for the calculation of the virtual dental prosthesis model, already existing data regarding the external shape of known artificial prosthesis teeth can be used.

With this measure, a repeated scanning or measuring of the physical prosthesis teeth used can be avoided, and therefore a further simplification of the method can be achieved.

The objects of the present invention are also solved by a dental prosthesis produced with such a method.

The objects underlying the invention are further solved by a device or combination of devices for carrying out such a method, comprising a CAM device and a computer for calculating the virtual models and controlling the CAM device.

Finally, the objects of the invention are also solved by a template produced with a CAD/CAM process for implementing such a method.

The physical prosthesis teeth, the physical template, as applicable the physical model of the oral cavity situation of patient, and/or the physical prosthesis base consist preferably of a plastic, particularly preferably of polymethyl methacrylate (PMMA), or are produced from this or with it.

The prosthesis teeth can be present individually and/or in a plurality of groups or assembled as complete rows of teeth. Assembled prosthesis teeth are securely connected to one another.

In the present situation, within the framework of the invention, the generally known term of the Rapid Prototyping process (RP process) is used for a production process with which the prosthesis base and the template are produced with a production process which is usual for Rapid Prototyping. Since the prosthesis base and the template are not prototypes but are finished or semi-finished components, it would also be possible to use, instead of the term "Rapid Prototyping process", the terms which are occasionally used in such contexts, "rapid manufacturing", "generative manufacturing process", "rapid product development", "advanced digital manufacturing", or "E-manufacturing". The prosthesis base is preferably produced from a pink-colored plastic, and, as appropriate, the prosthesis teeth from a plurality of tooth-colored plastics.

The cement or the adhesive for the permanent fixing of the prosthesis teeth in the prosthesis base should be non-toxic, volume-filling, color-fast, permanent as a compound, hydrolysis-resistant, and volume-stable when curing, as well as having a suitable color which is stable over a long period of time. Consideration can be given in this situation to, as well as PMMA cements such as Paladur® from Heraeus Kulzer GmbH, also Versyo® from Heraeus Kulzer GmbH, Signum composit Flow® from Heraeus Kulzer GmbH, or other PMMA-based cements.

As adhesive, it is possible to use, for example, a secondary adhesive, or an adhesive which is also suitable for filling a volume of intermediate spaces which might possibly occur between the prosthesis base and the prosthesis teeth.

The invention is based on the surprising finding that it is possible with the template to provide a matching form, in the manner of a three-dimensional puzzle piece, with which the positioning of the prosthesis teeth in the prosthesis base can be precisely achieved. For this purpose, the template is produced as a matching form to the external form of the prosthesis base which is to be produced and to the prosthesis teeth which are to be inserted, such that the prosthesis teeth are secured to the prosthesis base only in the desired alignment and position in relation to one another and in relation to prosthesis base. As a result, errors and effort in the positioning of the prosthesis teeth in the prosthesis base can be avoided. The template can in this situation be digitally designed with a CAD/CAM process from the virtual models of the prosthesis teeth and the prosthesis base, and then produced with a CAM process. The virtual models of the prosthesis teeth and of the prosthesis base necessary for this are in any event available with the production of the dental prosthesis with CAD/CAM processes, and can therefore be used without any great extra effort or expenditure.

With the method according to the invention, the form of an analog transfer key can now also be exploited by digital means, and generated as a separate data record in addition to the prosthesis base, the prosthesis teeth, and the model.

BRIEF DESCRIPTION OF THE DRAWINGS

Exemplary embodiments of the invention are explained hereinafter on the basis of five schematically represented figures, but without thereby restricting the invention. The figures show.

DETAILED DESCRIPTION

Figure 1:
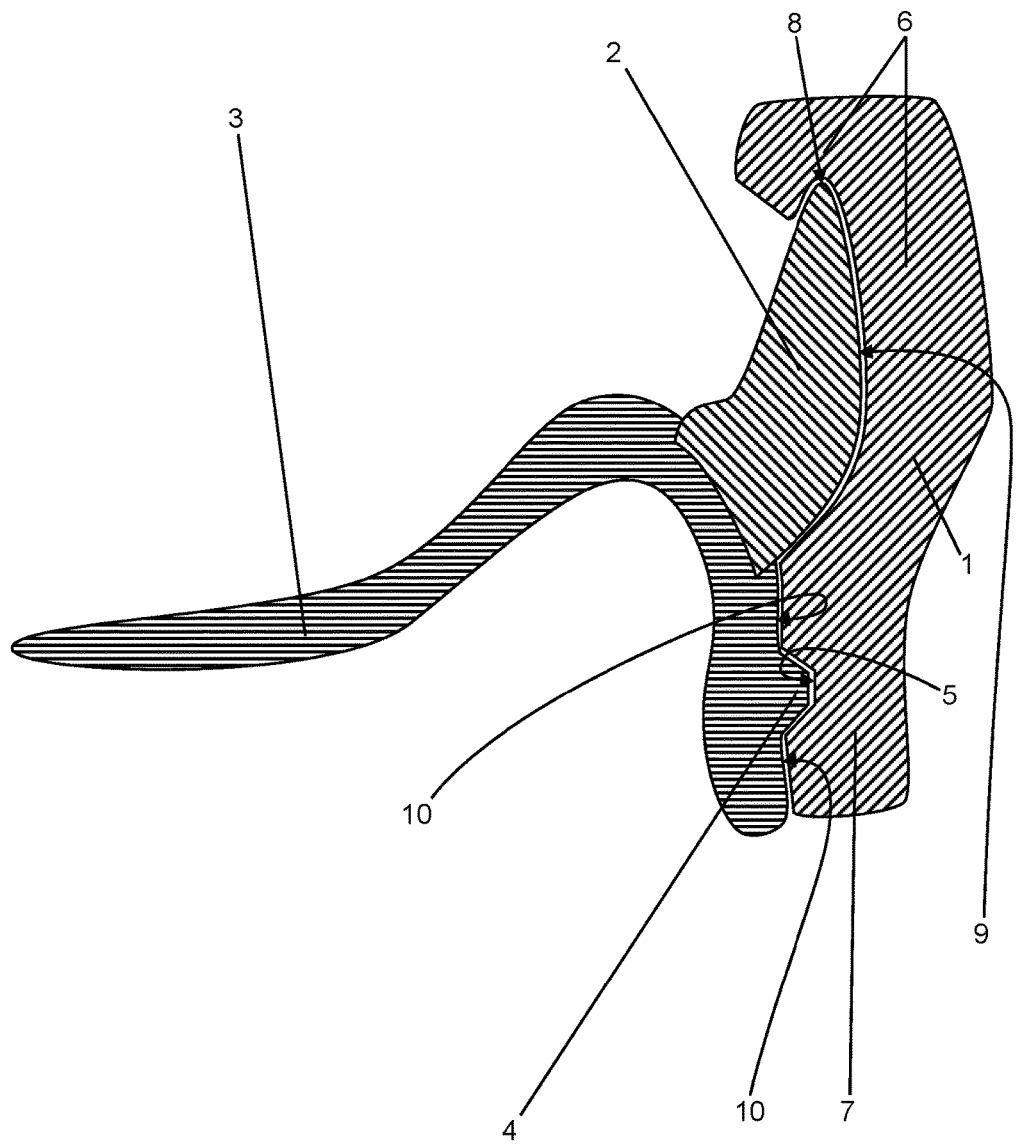
FIG. 1: a cross-section of a dental prosthesis with a template in place.

FIG. 1 shows a cross-section of a dental prosthesis a template 1 in place. The plane of the cross-section lies in the transversal plane of the patient, or is parallel to the transversal plane of the patient. The dental prosthesis comprises a plurality of prosthesis teeth 2 and a prosthesis base 3. The prosthesis teeth 2 are configured here as cutting teeth prostheses or incisors. The prosthesis teeth 2 are secured in matching tooth sockets in the prosthesis base 3, in that the prosthesis teeth 2 are inserted into the template 1, the prosthesis teeth 2 are wetted basally with an adhesive, as are the tooth sockets, and the prosthesis base 3 is then inserted into the template 1.

In order to ensure the desired orientation and location of the prosthesis teeth 2 in the prosthesis base 3 by a precise mounting of the template 1 on the prosthesis base 3, three indexings 4, 5 are provided on the template 1 and on the prosthesis base 3. On the prosthesis base 3, an elevation 4 is introduced as an indexing 4 or as a geometric shape respectively, which engages into an indentation 5 as an indexing 5 on the template 1. The result of this is that the template 1 with the prosthesis teeth 2 inserted can only be mounted in a specific orientation and location onto the prosthesis base 3, and therefore the prosthesis teeth 2 can be secured only in the orientation and location in the prosthesis base 3 as has been calculated in the dental prosthesis model.

The physical prosthesis base 3 consists of a pink-colored plastic. The coloring and transparency are selected such as to match the appearance of the gum. Provided in the prosthesis base 3, along the jaw arch, are a plurality of tooth sockets for the fixing of the prosthesis teeth 2. The prosthesis base 3 is produced by way of a virtual CAD model, which is derived by means of file-splitting from a virtual dental prosthesis model. In order to produce the real prosthesis base 3, the virtual CAD model of the prosthesis base 3 is produced with a CAM process, for example by printing or by milling out of a round or circular blank.

The virtual dental prosthesis model is produced first by an intraoral scan of the patient being carried out, or a scan of a plaster model of the oral cavity situation, or a scan of the impression of the oral cavity situation of the patient. Based on this data, a virtual arrangement of the prosthesis teeth 2 is prepared, wherein preferably the articulation of the patient's jaw is also taken into account. For this purpose, use can be made of virtual CAD models of artificial prosthesis teeth 2 which are to be used, which are arranged in a basic form of the virtual prosthesis base.

The template 1 is provided with a dental part 6, which is in contact with the prosthesis teeth 2, and a base part 7, which is in contact with the prosthesis base 3. The dental part 6 forms a negative of the occlusal or incisor surfaces 8 respectively, and of the vestibular surface 9 of the prosthesis teeth 2, aligned with one another on the basis of the dental prosthesis model, and the base part 7 forms a negative of the vestibular surface 10 of the prosthesis base 3, aligned with the prosthesis teeth 2 on the basis of the dental prosthesis model. The template 1 is produced with the aid of a CAD/CAM process, in that the external forms 8, 9, 10 are used of the virtual models of the prosthesis teeth 2, aligned in relation to one another and to the prosthesis base 3, as well as of the prosthesis base 3 itself, in order to calculate the form of a surface of the template 1 as a negative of the vestibular surface 10 of the prosthesis base 3 and of the vestibular surface 9 and occlusal surface 8 of the prosthesis teeth 2, and then to produce them. As a result of this, a precise match of the prosthesis teeth 2 and the prosthesis base 3 with the template 1 is achieved.

Figure 2:
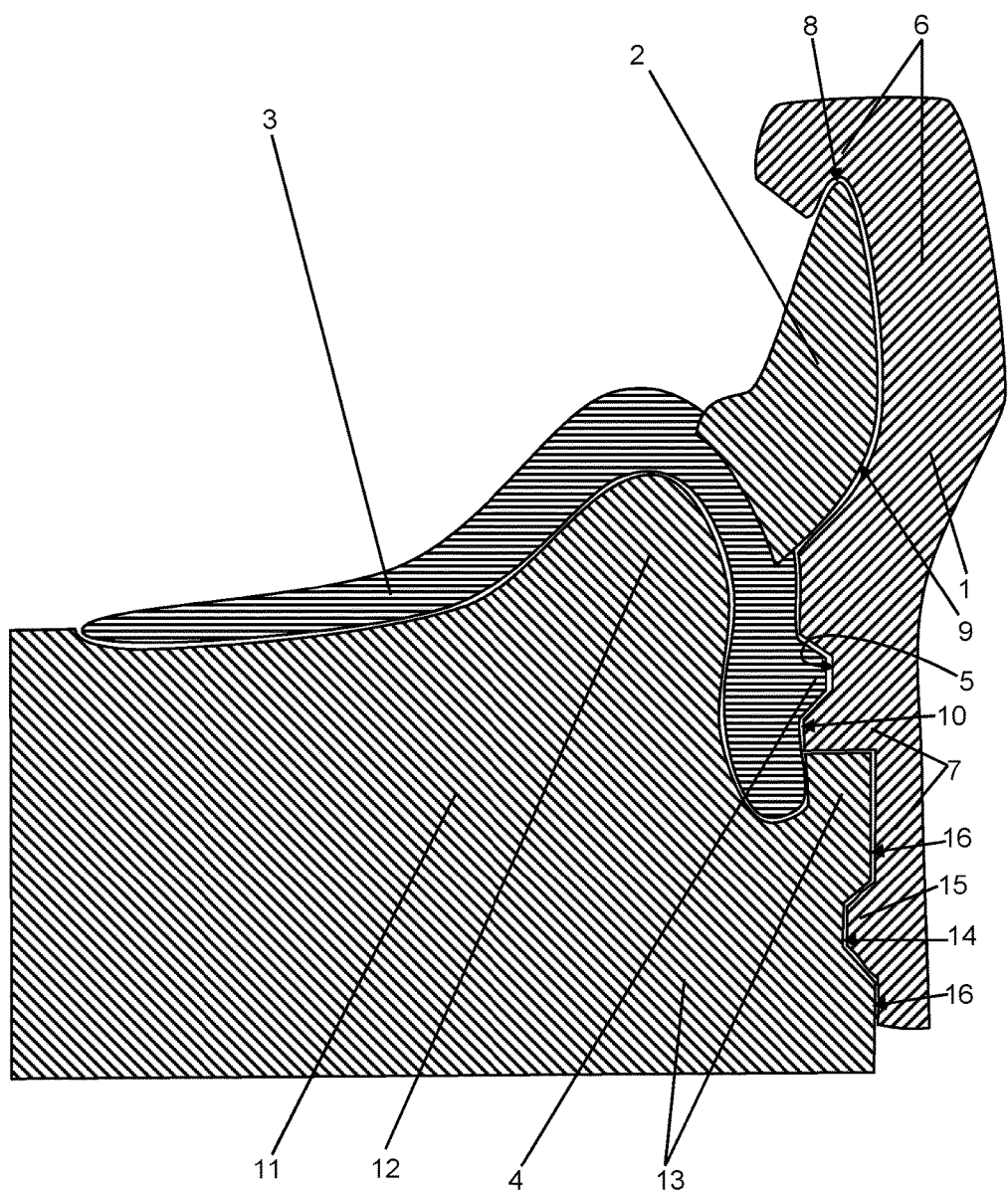
FIG. 2: a cross-section of a dental prosthesis with a template in place and with a model of the oral cavity of a patient.

FIG. 2 shows a cross-section of a dental prosthesis with the template 1 in place and with a model 11 in place of the oral cavity of a patient. The structural arrangement according to FIG. 2 resembles that according to FIG. 1, with the addition that the model 11 of the oral cavity situation of the patient is used in order to bring the structure together. The prosthesis base 3 lies on the model 11 of the oral cavity situation. Arranged on the jaw arch of the prosthesis base 3 are tooth sockets, into which the prosthesis teeth 2 are inserted.

In comparison with the structure according to FIG. 1, the template 1 projects further over, and partially covers, the vestibular surface 16 of the model 11 of the oral cavity situation. The model 11 of the oral cavity situation consists of an upper part 12, which represents a model of the toothless jaw arch 12 of the patient, and a base 13, which reflects a prolongation of the oral cavity situation, and which is not derived from the real anatomical circumstances of the patient. Provided in the vestibular surface of the model 11 of the oral cavity situation on the base 13 of the model 11 are three indentations 14 as indexings 14.

Provided at the template 1, in the region of the connection surface 16 to the model 11 of the oral cavity situation or, respectively, on the base part 7 of the template 1, are three indexings 15 as elevations 15, which match the indentations 14 in the model 11 of the oral cavity situation. As a result, the template 1 can be held and aligned not only by the indexing 5 and the indexing 4 on the prosthesis base 3, but also by means of the indexing 15 with the indexing 14 on the model 11 of the oral cavity situation.

Figure 3:
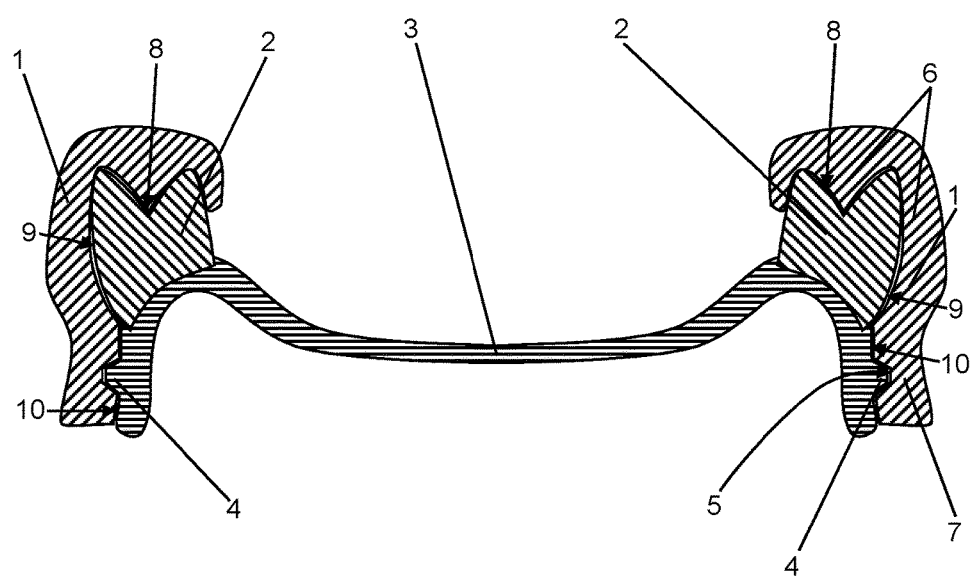
FIG. 3: a cross-section of a dental prosthesis with a template in place.

FIG. 3 shows a cross-section of a dental prosthesis with the template 1 in place, analogous to FIG. 1, wherein the section is represented parallel to a frontal plane. The sectioned prosthesis teeth 2 are configured here as molars or posterior or buccal teeth prostheses. The template 1 extends around the entire dental arch of the prosthesis teeth 2 and around the jaw arch of the prosthesis base 3. The two indexings 4 identifiable in the cross-section, on the prosthesis base 3, can be configured as rectangular or parallelepiped elevations 4, which engage into corresponding indentations 5 in the base 7 of the template 1. The indexings 4, 5 are not circumferential but geometrical forms which are delimited locally or around a single point.

The elevations 4 must be removed after the securing of the prosthesis teeth 2 with the aid of the template 1, in that, for example, they are abraded away. Any surplus residues can then be removed by polishing.

Figure 4:
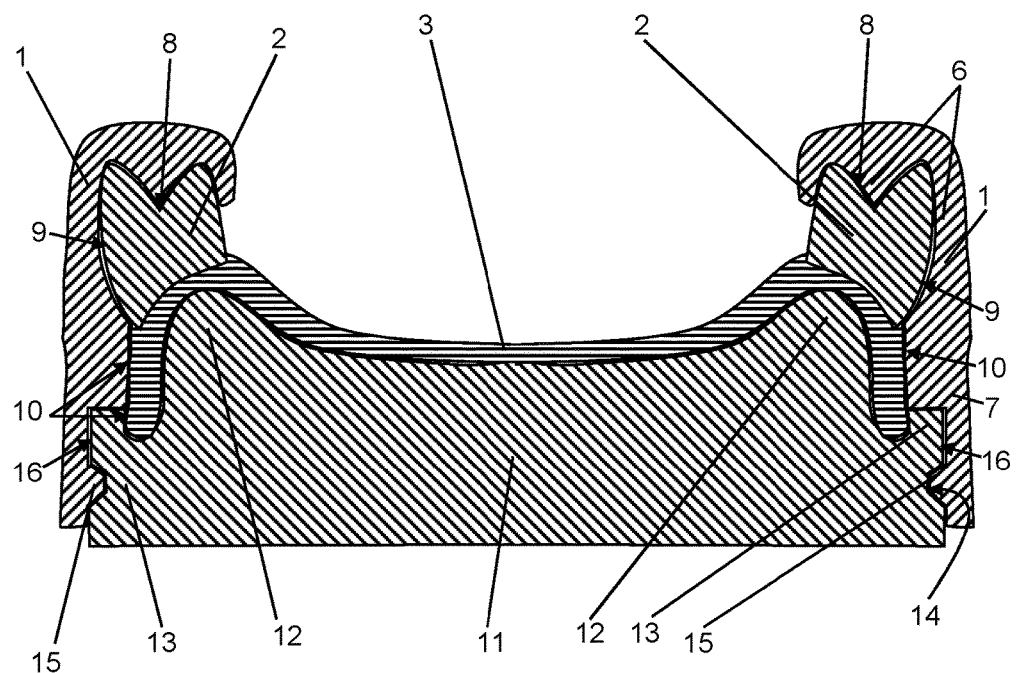
FIG. 4: a cross-section of a dental prosthesis with a template in place and with a model of the oral cavity of a patient.

The removal of the elevations 4 can be avoided if a model 11 of the oral cavity of the patient is used and corresponding indexings 14 are provided at the model 11, which engage into negative indexings 15 on the template 1, as is represented in FIG. 4, or as this would be analogously to FIG. 2 without the indexings 14, 15 on the prosthesis base 3. FIG. 4 shows in this context a cross-section parallel to the frontal place, in which the model 11 of the oral cavity situation is arranged beneath the prosthesis base 3. With this embodiment according to FIG. 4, the prosthesis base 3, by contrast with the exemplary embodiments according to FIGS. 1 to 3, does not exhibit any indexing. Accordingly, there is likewise no need to provide any indexing in the negative of the vestibular surface 10 of the prosthesis base 3 of the template 1. The alignment and orientation of the template 1 take place with this embodiment exclusively by way of indexings 14, 15 on the model 11 of the oral cavity situation and on the template 1, in the region which forms the negative to the vestibular surface 16 of the model 11 of the oral cavity situation or its base 13 respectively.

With all the embodiments the principle applies that the physical prosthesis teeth 2 are preferably present individually and are not connected to one another. The method according to the invention can, however, also be put into effect with rows of prosthesis teeth 2 connected to one another, either all or in groups.

The prosthesis teeth 2 consist of a hard white plastic, with a coloring and transparency which match teeth in general or the teeth of the patient. Each prosthetic tooth 2 comprises a basal surface, an occlusal surface 8, and a vestibular surface 9. The basal surface is fixed in the tooth sockets for fixing the prosthesis teeth 2 in the prosthesis base 3. The tooth sockets match the basal counterparts on the basal side of the prosthesis teeth 2. According to the invention, the basal side of the prosthesis teeth 4 is formed by basal abrading of artificial prosthesis teeth, in particular by grinding or milling.

The template 1 in all the exemplary embodiments is produced in that the form of the surface 8, 9 of all the coronal sides and vestibular surfaces of the prosthesis teeth 2 and of the vestibular surface 10 of the prosthesis base 3 is used, in the orientation and arrangement to one another from the virtual dental prosthesis model, as a CAD model for a surface of the template 1. The other surfaces of the CAD model of the template 1 can be easily automatically added as simple volume forms, or are formed additionally as negatives of the vestibular surface 16 of a model 11 of the oral cavity situation of the patient. In this situation it needs only to be ensured that the template 1 is not too thin, such that the mechanical durability of the template 1 is guaranteed. Theoretically, the template 1 can also consist of a plurality of parts, which accommodate the groups of prosthesis teeth 2 or individual prosthesis teeth 2.

The CAD model of the template 1 is used to produce the real template 1 with a CAM process, for example by an RP process, from plastic. The surfaces of the template 1, represented in section in the figures, exhibit accommodation surfaces which correspond to the coronal form 8 and the vestibular form 9 of the prosthesis teeth 2 which are to be inserted, and to the vestibular form 10 of the prosthesis base 3.

The prosthesis teeth 2 can be cleaned before securing to the prosthesis base 3, and in that situation can remain in the template 1 if appropriate. The prosthesis teeth 2 are first roughed on the basal side (for example mechanically by sandblasting or chemically with a suitable solvent agent) and/or swelled with a liquid containing methyl methacrylate (MMA). Likewise, the tooth sockets of prosthesis base 3 are roughed for the fixing of the prosthesis teeth 2 and swelled with a liquid containing MMA. As a liquid containing MMA, use can be made, for example, of Palabond® from Heraeus Kulzer GmbH.

Following the preparation in this way of the surfaces which are to be connected, a final cementing or adhesive bonding of the prosthesis teeth 2 in the prosthesis base 3 takes place, wherein the prosthesis teeth 2 initially still remain fixed in the template 1.

For the cementing, a cement can be used in excess, such that possible intermediate spaces between the tooth sockets for the fixing of the prosthesis teeth 2 in the prosthesis base 3 and the prosthesis teeth 2 will be filled with the cement, without basal cavities remaining in the intermediate spaces, and without peripheral gaps remaining in the region of the gingvia-cervis dentis. In addition, the excess will also optimally wet the contact surfaces. Excess cement paste residues incurring swelling can be removed before the curing and/or after the curing. For the final permanent securing of the prosthesis teeth 2 in the prosthesis base 3, preferably a self-curing cement on a powder-liquid base is used.

The method according to the invention can be carried out with prosthesis bases 3 or models 11 of the oral cavity, produced manually or by means of Rapid Prototyping processes. Likewise, the method can alternatively also be applied to printed prosthesis teeth or prosthesis teeth rows.

Figure 5:
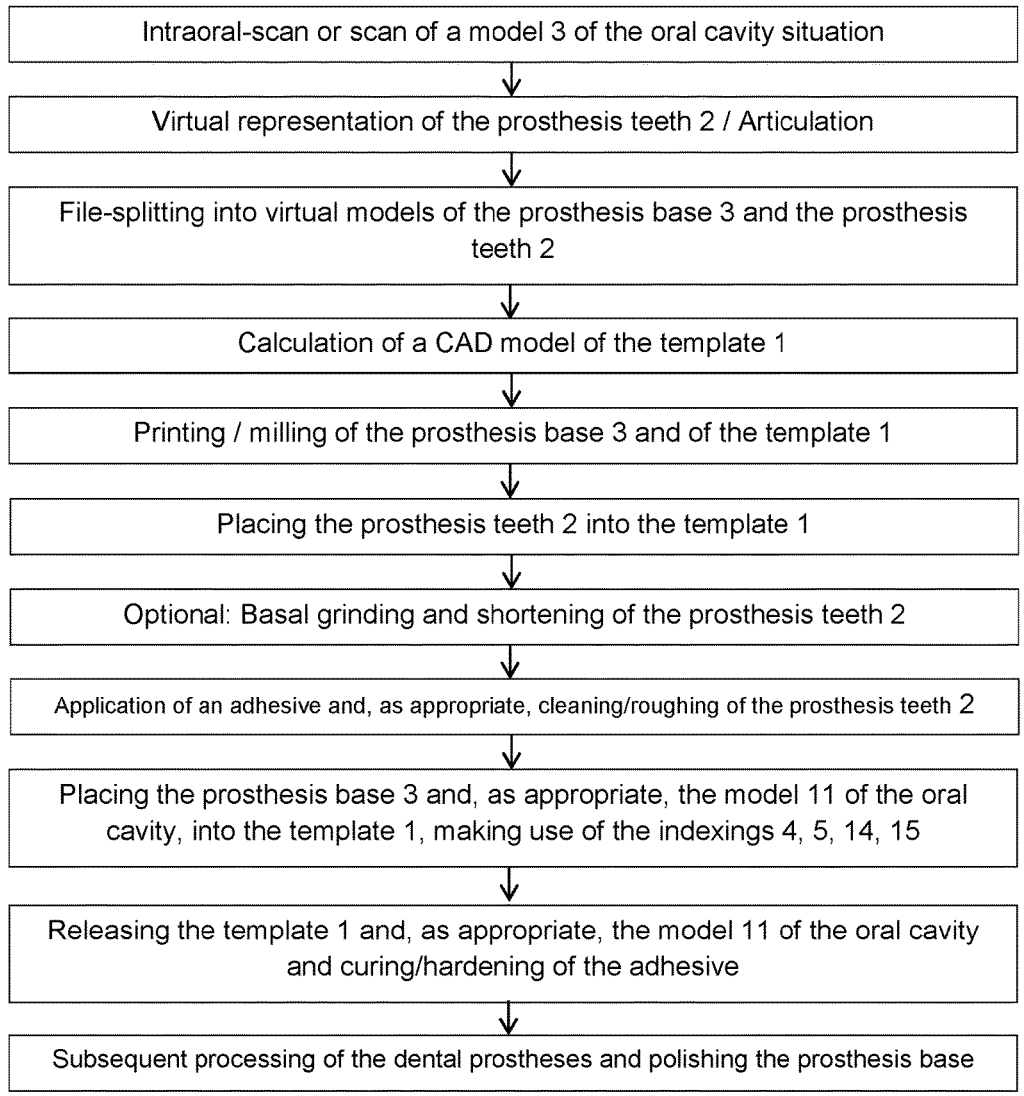
FIG. 5: an exemplary sequence diagram for a method according to the invention.

Shown in FIG. 5 is an exemplary sequence diagram for a method according to the invention.

Optionally, the real prosthesis teeth 2 can be produced and/or processed by manufacturing or shortening with a CAM process.

According to the invention, the objects underlying the present invention are therefore solved, for example, in that, based on an intraoral scan or the scan of an impression (such as of a plaster model, for example) of the toothless or partially toothless jaw, first a virtual dental prosthesis is digitally designed and constructed, and then, by means of file-splitting, is divided into one part for the prosthesis base 3 and one part for the prosthesis teeth 2.

For the positioning of the prosthesis teeth 2, a template 1 is now produced by means of RP processes (such as milling or printing), in order to be able to fix the prosthesis teeth 2 exactly in this previously determined spatial arrangement and to transfer it onto the prosthesis base 3.

In order to be able to place and align the prosthesis teeth 2 in the prosthesis base 3 in the way as provided for in the CAD design data, it is proposed according to the invention that in the CAD process, automatically or supported by the user, a template 1 be constructed, which ensures the alignment of the prosthesis teeth 2 to the prosthesis base 3. This template 1 is likewise derived from the CAD process as a data record together with the data for the prosthesis base 3 and the prosthesis teeth 2, and is therefore available for an additive or subtractive production process.

The template 1 itself is designed for this purpose as an exact fit to the vestibular/buccal, occlusal/incisor surfaces of the prosthesis teeth 2, an exact fit to the vestibular/buccal surface of the prosthesis base 3, and/or an exact fit to the periphery of the model 11 of the oral cavity.

In this situation, for example, the following two variants of the method can be realized:

a) Use of the prosthesis base 3 for the alignment (without a physical model 11 of the oral cavity situation of the patient)

Because the surface of the prosthesis base 3 is anatomically designed, and is therefore rounded and does not exhibit any straight surfaces or corners for support and alignment, it is proposed that at several points, at least at three points, geometric forms 4 be provided as indexings 4 at the prosthesis base 3, and that these be produced jointly with the additive or subtractive method. For this purpose, the possibility must be provided in the CAD for the positioning of fixing aids 4 (CAD library with suitable geometries), which are then placed at suitable fixing points on the prosthesis base 3.

The geometry of the template 1 is now to be arranged such that the upper portion 6 reproduces the forms 8, 9 and the arrangement of the prosthesis teeth 2, and the lower portion 7 allows for the alignment to the prosthesis base 3. For this purpose it must be ensured that the template 1 can be aligned exactly to the prosthesis base 3, such that the position is determined in all spatial directions. For this a minimum of three fixed points are necessary.

The template 1 is then supported and fixed by way of these geometrical arrangements 4. After the alignment and fixing of the prosthesis teeth 2 in the prosthesis base 3, these geometric shapes 4 on the prosthesis base 3 are removed by the dental technician with a manual milling device and smoothed out during polishing, which is carried out in any event for the final completion of the dental prosthesis.

b) Use of the model 11 of the oral cavity situation of the patient for alignment For the better fixing of the template 1 on the model 11, it must be provided before the scan process with possibilities for fixing (for example with guidance grooves, notched, or troughs).

The geometry of the template 1 is now arranged in such a way that the upper portion 6 reproduces the forms 8, 9 and the arrangement of the prosthesis teeth 2, and the lower portion 7 allows for the alignment to the prosthesis base 3, in that corresponding geometries 15 of the template 1 are set into the fixing possibilities 14 of the model 11. For this purpose it must be ensured that the template 1 can be aligned precisely on the model 11, such that the position is secured in all spatial directions. For this a minimum of three fixed points are necessary.

The transfer template 1 is then supported and fixed by means of the fixing possibilities 15 in the model 11, and allows for the prosthesis teeth 2 to be set aligned into the prosthesis base 3 and fixed. As soon as the prosthesis teeth 2 are firmly secured, the template 1 can be removed. Manual subsequent processing of the prosthesis base 3 as under a) is not necessary if no indexings are additionally provided on the prosthesis base 3.

It would also be conceivable for a fixing arrangement to be introduced equally in the model 11 and in the prosthesis base 3. This is not absolutely necessary for the function, however, and incurs the condition that the geometric forms 4 would have to be removed again from the prosthesis base 3, as described under a).

The features of the invention as disclosed in the foregoing description, as well as in the claims, figures, sequence diagram, and exemplary embodiments can be seen as substantial, both individually as well as in any desired combination, for the realization of the invention in its different embodiments.

REFERENCE NUMBER LIST

1 Template
2 Prosthesis tooth
3 Prosthesis base
4 Indexing/elevation
5 Indexing/indentation
6 Dental part of template
7 Base part of template
8 Occlusal surface of the prosthesis
9 Vestibular surface of the prosthesis tooth
10 Vestibular surface of the prosthesis base
11 Model of the oral cavity situation
12 Model of the dental arch
13 Base of the model of the oral cavity
14 Indexing/indentation
15 Indexing/elevation
16 Vestibular surface of the model of the oral cavity situation

The invention claimed is:

1. Method for producing a physical dental prosthesis, wherein the dental prosthesis comprises a physical prosthesis base and a plurality of physical prosthesis teeth, wherein the method is carried out using a virtual three-dimensional dental prosthesis model of the physical dental prosthesis which is to be produced and wherein the virtual three-dimensional dental prosthesis model comprises virtual prosthesis teeth and a virtual prosthesis base, the method comprising the following chronological steps:

A) calculating a virtual model of a template from an external shape of vestibular surfaces and/or occlusal surfaces of the virtual prosthesis teeth and from an external form of a vestibular surface of the virtual prosthesis base of the virtual three-dimensional dental prosthesis model, to form a region of a virtual surface of the virtual template by a negative of the vestibular surfaces and/or occlusal surfaces of the virtual prosthesis teeth and of the virtual prosthesis base, wherein a location and an orientation of the virtual prosthesis teeth relative to one another and relative to the virtual prosthesis base are retained in the negative;

B) producing a physical template with a CAM process on the basis of data of the virtual model of the template;

C) placing and securing physical prosthesis teeth in the physical template, wherein the vestibular surfaces and/or occlusal surfaces of the physical prosthesis teeth are placed in a surface of the physical template which is formed by the matching negative; and D) securing the physical prosthesis teeth to a physical prosthesis base, wherein the physical prosthesis base is inserted into the physical template fitted with the physical prosthesis teeth, such that the vestibular surface of the physical prosthesis base is located on the matching surface of the physical template formed by the matching negative.

2. Method according to claim 1, comprising dividing the virtual three-dimensional dental prosthesis model by computer calculation by file-splitting into a three-dimensional model of the virtual prosthesis teeth and a virtual three-dimensional model of the prosthesis base.

3. Method according to claim 1, comprising additionally calculating the virtual model of the template from an external form of a vestibular surface of a model of an oral cavity situation of a patient, such that a region of the virtual surface of the virtual template is formed by a negative of at least one region of the vestibular surface of the model of the oral cavity situation, wherein the location and the orientation of the virtual prosthesis teeth and of the virtual prosthesis base, relative to the model of the oral cavity situation, with the virtual prosthesis base lying on the model of the oral cavity situation, are retained in the negative.

4. Method according to claim 3, comprising, in step D), securing the physical prosthesis teeth to the physical prosthesis base in such that the physical prosthesis base and the physical model of the oral cavity situation of the patient are inserted into the physical template fitted with the prosthesis teeth, such that the vestibular surface of the physical prosthesis base and the vestibular surface of the physical model of the oral cavity of the patient are in contact with the physical surface of the template formed by the negative.

5. Method according to claim 3, comprising adding to the negative of the vestibular surface of the model of the oral cavity situation, by computer calculation, at least one indexing to the virtual model of the template, and adding to the vestibular surface of the model of the oral cavity situation, by computer calculation, a matching negative of the surface of the at least one indexing to the model of the oral cavity situation.

6. Method according to claim 1, comprising adding to the negative of the vestibular surface of the virtual prosthesis base, by computer calculation, at least one indexing and adding to the vestibular surface of the virtual prosthesis base, by computer calculation, a matching negative of the surface of the at least one indexing.

7. Method according to claim 1, comprising, after step D), removing the physical template of the finished dental prosthesis, including the prosthesis teeth secured in the prosthesis base.

8. Method according to claim 1, comprising producing the virtual three-dimensional dental prosthesis model on the basis of an intraoral scan for determining the form of the virtual prosthesis base and by a virtual arrangement of virtual models of prefabricated artificial prosthesis teeth in the virtual prosthesis base.

9. Method according to claim 1, comprising producing and/or processing the physical prosthesis base and the physical template by CAM processes based on the virtual models.

10. Method according to claim 1, comprising basally processing the physical prosthesis teeth inserted into the physical template before they are secured to the physical prosthesis base.

11. Method according to claim 10, comprising basally abrading the physical prosthesis teeth on the basis of the virtual model of the prosthesis teeth by a CAM process such that a basal form of the physical prosthesis teeth is adjusted to tooth sockets for the physical prosthesis teeth in the physical prosthesis base, and wherein an outer form of the physical prosthesis base, with the physical prosthesis teeth inserted, corresponds to an outer form of the virtual dental prosthesis model.

12. Method according to claim 1, comprising producing the prosthesis teeth with a CAM process.

13. Method according to claim 1, comprising using existing data regarding an external form of known prefabricated artificial prosthesis teeth to calculate the virtual dental prosthesis model.

14. Dental prosthesis produced with a method according to claim 1.

15. Device or combination of devices for carrying out a method according to claim 1, comprising a CAM device and a computer for calculating the virtual models and controlling the CAM device.

16. Template produced with a CAD/CAM process for implementing a method according to claim 1.

17. Method according to claim 5, comprising adding to the negative of the vestibular surface of the model of the oral cavity situation, by computer calculation, at least three indexings to the virtual model of the template, and adding to the vestibular surface of the model of the oral cavity situation, by computer calculation, matching negatives of the at least three indexings to the model of the oral cavity situation.

18. Method according to claim 6, comprising adding to the negative of the vestibular surface of the virtual prosthesis base, by computer calculation, at least three indexings, to the virtual model of the template, and adding to the vestibular surface of the virtual prosthesis base, by computer calculation, matching negatives of the at least three indexings.

19. Method according to claim 8, comprising producing the virtual three-dimensional dental prosthesis model on the basis of an intraoral scan for determining the form of the virtual prosthesis base and by a virtual arrangement of virtual models of prefabricated artificial prosthesis teeth in the virtual prosthesis base, wherein the form, the location, and/or the orientation of the prosthesis teeth are selected by a simulating the location of the dental prosthesis in the oral cavity of the patient, and/or by simulating the location and orientation of the prosthesis teeth in relation to one another and/or to the prosthesis base.

20. Method according to claim 19, comprising simulating an occlusion plane and/or mastication movements of the oral cavity.

21. Method according to claim 9, comprising producing and/or processing the physical prosthesis base and the physical template by Rapid Prototyping CAM processes based on the virtual models.

22. Method according to claim 1, comprising basally abrading prefabricated artificial prosthesis teeth by a CAM process, based on the virtual model of the prosthesis teeth inserted into the physical template before they are secured to the physical prosthesis base.

23. Method according to claim 22, comprising basally abrading the prefabricated artificial prosthesis teeth by a computer-controlled milling process before they are secured to the physical prosthesis base.

24. Method according to claim 11, comprising basally abrading the physical prosthesis teeth on the basis of the virtual model of the prosthesis teeth by a CAM milling process.

25. Method according to claim 12, comprising producing the prosthesis teeth with a CAM milling process or a building up CAM process.

* * * * *